United States Patent [19]

Kuhlmann et al.

[11] Patent Number: 4,837,110

[45] Date of Patent: Jun. 6, 1989

[54] TECHNETIUM-99M GENERATOR, ITS PREPARATION AND ITS USE

[75] Inventors: Ludwig Kuhlmann, Hofheim am Taunus; Dietrich Pütter, Frankfurt am Main, all of Fed. Rep. of Germany

[73] Assignee: Hoechst Aktiengesellschaft, Frankfurt am Main, Fed. Rep. of Germany

[21] Appl. No.: 214,889

[22] Filed: Jun. 29, 1988

Related U.S. Application Data

[63] Continuation of Ser. No. 901,881, Aug. 29, 1986, abandoned.

[30] Foreign Application Priority Data

Sep. 3, 1985 [DE] Fed. Rep. of Germany ....... 3531355

[51] Int. Cl.[4] ...................... G21G 4/08; C01G 57/00; A61K 43/00

[52] U.S. Cl. ........................................ 423/2; 424/1.1; 252/645; 210/682; 250/432 PD

[58] Field of Search ........................ 424/1.1; 252/645; 250/432 PD; 423/2, 249, 49; 210/682, 679

[56] References Cited

U.S. PATENT DOCUMENTS

| | | | |
|---|---|---|---|
| 3,369,121 | 2/1968 | Bruno et al. | 250/106 |
| 3,664,964 | 5/1972 | Haney et al. | 252/364 |
| 3,740,558 | 6/1973 | Kato et al. | 250/432 PD |
| 3,755,161 | 8/1973 | Yokota et al. | 210/36 |
| 4,158,700 | 6/1979 | Karageozian | 423/2 |
| 4,167,481 | 9/1979 | Cremers et al. | 210/36 |
| 4,414,145 | 11/1983 | Panek | 252/645 |

FOREIGN PATENT DOCUMENTS

| | | | |
|---|---|---|---|
| 0014957 | 9/1980 | European Pat. Off. | 424/1.1 |
| 8533473 | 3/1986 | Fed. Rep. of Germany . | |
| 1186587 | 4/1970 | United Kingdom . | |

*Primary Examiner*—John F. Terapane
*Assistant Examiner*—Virginia Caress
*Attorney, Agent, or Firm*—Finnegan, Henderson, Farabow, Garrett & Dunner

[57] ABSTRACT

Silica gels modified with amino groups or magnesium silicates are suitable carrier materials for technetium-99m generators since they retain copper(II) ions well and thus produce a copper-free eluate.

20 Claims, 1 Drawing Sheet

TECHNETIUM-99M GENERATOR, ITS PREPARATION AND ITS USE

Figure 1:
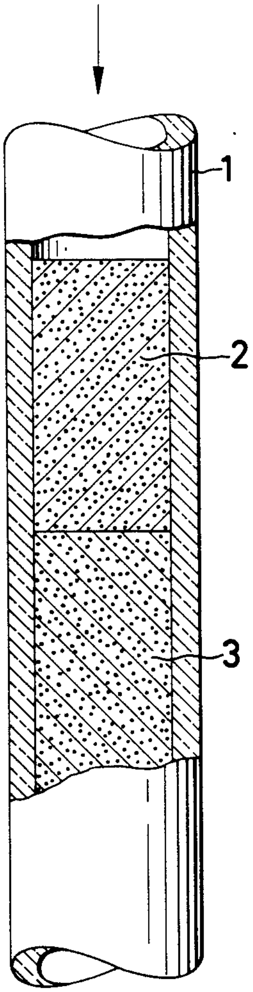

This application is a continuation of application Ser. No. 901,881, filed Aug. 29, 1986 now abandoned.

The invention relates to an improved technetium-99m generator based on molybdenum-99 adsorbed on a carrier, a process for the preparation of such generators and their use for obtaining eluates containing technetium-99m in the form of pertechnetate.

Technetium-99m is the most frequently used radioactive nuclide in nuclear medicine diagnostics. This is because of its optimum nuclear physical properties for this application (short half-life of 6.0 hours, no corpuscular radiation and an advantageous $\gamma$-energy of 140 keV). It can be obtained easily and simply from a molybdenum-99/technetium-99m generator.

In the type of generator most widely used at present, the molybdenum-99, from which the isotope technetium-99m is continuously formed by nuclear decay, is adsorbed onto an aluminum oxide column as molybdenum-99 molybdate. The technetium-99m, which is present chemically as pertechnetate, is separated off from the molybdenum-99 by washing with isotonic sodium chloride solution. So-called fission molybdenum is today used almost exclusively as the molybdenum-99. It is isolated from the fission product mixture obtained on nuclear decay of uranium-235 and has a very high specific activity. It is thereby possible to obtain high technetium-99m activities in small volumes of sodium chloride solution from a generator.

The introduction of fission molybdenum enabled only small amounts (1–2 g) of aluminum oxide to be used in the generators, which meant that the minimum amount of sodium chloride solution necessary to elute the technetium-99m could be limited to a few milliliters (about 5 ml).

The minimum requirements to be imposed on a ready-to-use generator are summarized in DIN 6854 (January 1985). According to this, the elutable activity of Tc-99m should not fall below 70% on elution at 24 hour intervals. The quality of the eluate is thereby subject to certain requirements. It is of course desirable to keep below these limit values as far as possible. This particularly applies to molybdenum-99, which the generator contains in high activities and which, in the eluate, would lead to unnecessary exposure to radiation when used on humans because of the long half-life of 66.0 hours.

It is known that Mo-99/Tc-99m generators with fission molybdenum, in particular with relatively high Mo-99 activities, tend towards losses in yield or sometimes even to breakdowns in yield (European Pat. No. B-0,014,957). This effect is intensified further by organic impurities in the eluting agent, which, for example, can pass into the sodium chloride solution from eluting agent vessels made of plastic.

In order to avoid these losses in yield, yield stabilizers are used. It is known that copper(II) ions have this stabilizing effect.

However, the difficulty arises here that the small amounts of aluminum oxide are not sufficient to prevent passage of the copper into the eluate in the long term.

German Offenlegungsschrift No. 1,929,067 describes the addition of copper(II) acetate to the eluting agent. 0.001 percent by volume is required as the minimum amount, which, certainly in the case of copper(II) acetate, is to be understood as 10 $\mu$g/ml=3.5 $\mu$g of Cu(II)/ml. For modern generators which, in contrast to those which were customary on priority date of the German Offenlegungsschrift mentioned, contain only a small amount of aluminum oxide, this is not sufficient—even when the minimum copper(II) concentrations mentioned are used—to prevent the copper from passing into the eluate, as referred to. Moreover, it has been found that 3.5 $\mu$g of Cu(II)/ml of eluting agent cannot always guarantee a constantly high yield.

To prevent passagte of copper ions into the eluate, European Pat. No. B-0,014,957 has described a process which permits fixing of relatively large amounts of copper(II) onto the aluminum oxide. However, this method requires an additional process step in the preparation of the generators and is thus expensive.

It has now been found that magnesium silicates, and silica gels modified with amino groups are advantageous carrier materials for technetium-99m generators which are capable of firmly bonding copper(II) ions. The invention thus relates to technetium-99m generators based on molybdenum-99 adsorbed on a carrier, which contain a magnesium silicate and/or a silica gel modified with amino groups.

It has furthermore been found that the silica gel modified with amino groups is capable of adsorbing radioactive molybdenum-99. The Mo-99 contents in the eluate can thus be reduced to less than 1 $\mu$Ci of Mo-99/Ci of Tc-99m. One embodiment of the invention thus reates to a technetium-99m generator, the carrier material of which consists of silica gel modified with amino groups. Preferred embodiments of this invention additionally contain, however, aluminum oxide.

Generators according to the invention which are based on magnesium silicate additionally contain aluminum oxide for adsorption of the Mo-99. For such generators which contain more than one carrier material, it is in principle possible to mix the carrier materials and to fill the customary apparatuses with the mixture. However, since the different materials in general have a different particle size, it must be ensured by special measures, for example by grinding them together, that no "channels" remain open in the filling. It is therefore in general more advantageous to fill the generators with different materials in layers. "In layers" here can mean that the different materials are introduced in several layers in alternating sequence, but it is advantageous to introduce each material in the form of a single layer.

It is in principle possible to use both a magnesium silicate and a silica gel modified with amino groups in one generator. In general, however, only one of the two materials will be used.

The magnesium silicate or the silica gel modified with amino groups is preferably introduced into the generator column as the bottom layer. A layer of aluminum oxide is then applied on top.

The invention described in European Pat. No. B-0,014,957 can also be utilized, in that a generator is prepared in which the aluminum oxide laden with copper(II) is introduced in the top layer, below this is a layer of aluminum oxide and underneath this follows a layer of the carrier material according to the invention.

Figure 2:
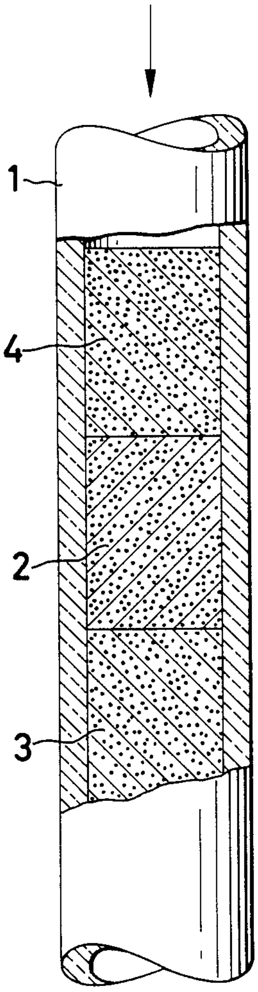

Two embodiments of the invention are shown in schematic and not necessarily dimensionally accurate form in FIGS. 1 and 2:

In FIG. 1, (1) is the column into which the carrier material is introduced, the elution direction (from the top downwards) being indicated by the arrow. (2) and (3) are the layers of different carrier materials, that is to say in a preferred embodiment aluminum oxide as layer (2) and magnesium silicate, or silica gel modified with amino groups as layer (3).

FIG. 2 shows a corresponding arrangement with three layers, three different materials (2), (3) and (4) being used. In a preferred embodiment of this aspect of the invention, (4) is a layer of aluminum oxide laden with copper(II), (2) is aluminum oxide and (3) is magnesium silicate, or silica gel modified with amino groups.

The technical development of nuclide generators is known and is described, for example, in German Auslegeschrift No. 1,614,486 (and the corresponding U.S. Pat. No. 3,369,121) or in British Pat. No. 1,186,587. Details can therefore be omitted here.

The amounts of carrier material depend on the dimensions of the generator and on the charging; they can easily be determined by simple preliminary experiments.

Suitable magnesium silicates are naturally occurring products, such as forsterite, enstatite, serpentine, serpentine asbestos, talc, antigorite or meerschaum, and corresponding synthetic products which contain magnesium orthodi- or polysilicates, the latter with a chain, belt or layer (leaf) structure. Such materials are employed, for example, for chromatographic processes.

Silica gels modified with amino groups are likewise customary carrier materials for chromatographic processes. A preferred form contains the amino groups in the form of 1,3-propylamine groups. However, other carrier materials, for example those with secondary or tertiary amino groups, such as are used as adsorbents for acid compounds, are also possible.

The invention is illustrated in more detail in the following examples.

The following carrier materials were used for the preparation of generator columns: aluminum oxide S, acid, superactive; Riedel de Haen; ®Florisil for column chromatography, Merck, "Mg silicate" below; ®LiChroprep $NH_2$ for liquid chromatography, Merck, "silica gel" below. Physiological sodium chloride solution containing different amounts of copper(II) chloride dihydrate was used as the eluting agent. The copper(II) was determined colorimetrically, the lower detection limit being 0.1 ppm.

EXAMPLE 1

The extent to which the carrier materials are capable of retaining copper(II) ions was determined by elution under identical conditions. Eluates No. 1–8 were free from copper in all cases. As shown byb the following Table 1, the magnesium silicate and the silica gel can trap the copper(II) very much better than the aluminum oxide.

TABLE 1

| Carrier material | $CuCl_2 \times 2H_2O$ in the eluting agent | Copper(II) contents in 13 ml of eluate (ppm) Eluate No. 9 | 10 | 11 | 12 | 13 |
|---|---|---|---|---|---|---|
| (a) 1.2 g of $Al_2O_3$ | 10 ppm | — | — | ~0.2 | ~0.5 | 1 |
| | 15 ppm | ~0.2 | ~0.5 | 1 | 1 | |
| (b) 530 mg of Mg silicate | 10 ppm | — | — | — | — | — |
| | 15 ppm | — | — | — | — | — |
| | 30 ppm | — | — | — | — | — |
| | 50 ppm | — | — | — | — | — |
| (c) 500 mg of silica gel | 50 ppm | — | — | — | — | — |
| | 100 ppm | — | — | — | — | — |
| (d) 1.0 g of $Al_2O_3$(1) | 15 ppm | — | — | — | — | — |
| (d) 150 mg of Mg silicate | 20 ppm | — | — | — | — | — |
| | 30 ppm | — | — | — | — | — |
| (e) 950 mg of $Al_2O_3$(1) | 30 ppm | — | — | — | — | — |
| 150 mg of silica gel | 40 ppm | — | — | — | — | — |
| | 50 ppm | — | — | — | — | — |

(1)The columns were charged with 0.5 mg of ammonium molybdate before elution with copper-containing sodium chloride solution.

EXAMPLE 2

A glass column is packed with 150 mg of Mg silicate and this is covered with a layer of 900 mg of aluminum oxide. The column is charged with Mo-99 and eluted each working day with physiologicaln sodium chloride solution containing 20 $\mu g$ of $CuCl_2 \times 2H_2O$ per ml. Before addition of the copper(II) chloride, the sodium chloride solution was sterilized in an autoclave together with the PVC foil usually employed for packaging. It is known that organic impurities which can lead to severe reductions in yield thereby pass into the eluting agent. For comparison, a column which contains only aluminum oxide and was eluted with copper(II)-free eluting agent was investigated. The result is shown in Table 2.

TABLE 2

| | | Elution days 1 Friday | 2 Monday* | 3 Tuesday | 4 Wednesday | 5 Thursday | 6 Friday | 7 Monday | 8 Tuesday | 9 Wednesday | 10 Thursday |
|---|---|---|---|---|---|---|---|---|---|---|---|
| Comparison generator 676 mCi of Mo-99 on the CD* | Yield of Tc-99m in % based on the Mo-99 activity at the time of elution | 69.7 | 80.1 | 45.2 | 37.2 | 31.0 | 27.6 | 36.9 | 17.4 | 10.7 | 8.0 |
| Test generator 676 mCi of Mo-99 on the CD* | Yield of Tc-99m in % | 77.0 | 83.8 | 74.6 | 75.9 | 76.0 | 74.7 | 82.6 | 72.8 | 72.6 | 72.4 |
| | Copper (II) content in the eluate in ppm | — | — | — | — | — | — | — | — | — | — |

*CD = Calculation day = elution day No. 2, Monday

Whilst the comparison generator shows a clear breakdown in yield, this has been prevented in the test generator according to the invention by the addition of copper(II), without noticeable amounts of copper(II) being present in the eluate.

EXAMPLE 3

105 mg of silica gel are introduced into a glass column and covered with a lyer of 1.0 of aluminum oxide. The generator columns are charged with Mo-99 and eluted each working day. Copper(II) chloride dihydrate is added to the eluting agent charged with organic impurities (see Example 2).

TABLE 3

| Generators | $CuCl \times 2\ H_2O$ in the eluting agent | Measurement parameter | Elution days 1 Friday | 2 Monday | 3 Tuesday | 4 Wednesday | 5 Thursday | 6 Friday | 7 Monday | 8 Tuesday | 9 Wednesday | 10 Thursday |
|---|---|---|---|---|---|---|---|---|---|---|---|---|
| Comparison generator (only $Al_2O_3$) | — | Yield of Tc-99m | 69.7 | 80.1 | 45.2 | 37.2 | 31.0 | 27.6 | 36.9 | 17.4 | 10.7 | 8.0 |
| 676 mCi of Mo-99 on the CD | | Mo-99 (ppm) | 1 | 1 | 1 | 1 | 3 | 2 | 12 | 4 | 7 | 10 |
| Test generator $Al_2O_3$ + silica gel | — | Yield of Tc-99m | 43.2 | 87.7 | 78.0 | 78.6 | 78.9 | 78.8 | 85.6 | 55.6 | 23.4 | 14.1 |
| 681 mCi of Mo-99 on the CD | | Mo-99 (ppm) | 1 | <1 | <1 | <1 | <1 | <1 | <1 | <1 | <1 | 2 |
| 677 mCi of Mo-99 on the CD | 20 ppm* | Yield of Tc-99m | 77.1 | 85.5 | 77.1 | 76.9 | 78.4 | 77.4 | 85.0 | 76.9 | 76.3 | 76.2 |
| | | Mo-99 (ppm) | 1 | 1 | <1 | <1 | <1 | <1 | <1 | <1 | <1 | <1 |
| 679 mCi of Mo-99 on the CD | 20 ppm* | Yield of Tc-99m | 77.5 | 85.4 | 76.6 | 76.4 | 75.9 | 76.1 | 82.9 | 76.7 | 77.0 | 76.9 |
| | | Mo-99 (ppm) | 1 | 1 | <1 | <1 | <1 | <1 | <1 | <1 | <1 | <1 |
| 688 mCi of Mo-99 on the CD | 30 ppm* | Yield of Tc-99m | 77.1 | 84.3 | 77.5 | 77.6 | 77.6 | 77.6 | 85.0 | 75.3 | 73.9 | 73.8 |
| | | Mo-99 (ppm) | <1 | 1 | <1 | <1 | <1 | <1 | <1 | <1 | <1 | <1 |
| 679 mCi of Mo-99 on the CD | 30 ppm* | Yield of Tc-99m | 78.0 | 85.6 | 77.7 | 77.5 | 78.0 | 78.5 | 84.9 | 77.1 | 76.8 | 76.0 |
| | | Mo-99 (ppm) | <1 | <1 | <1 | <1 | <1 | <1 | <1 | <1 | <1 | <1 |

CD = calculation day = elution day No. 2, Monday
*Cu(II) was not to be found in any eluate.

For comparison, a glass column was filled with 1.2 g of aluminum oxide, and another was filled with 105 mg of silica gel and 1.0 of aluminum oxide. These comparison generators were eluted with copper-free eluting agent charged with organic impurities.

The content of technetium-99M and molybdenum-99 and, if the eluting agent contains copper(II), the content of copper(II) is measured in the eluates. The results are summarized in Table 3. The yield of Tc-99m is given in %, based on the Mo-99 activity, the molybdenum-99 content is given in ppm, based on the Tc-99m activity, and the copper(II) content is given in ppm.

Table 3 shows:

1. By using silica gel, the Mo-99 content in the eluate is reduced to less than 1 ppm.
2. By using silica gel, copper(II) can be added to the eluting agent, the yield of Tc-99m remaining uniformly high without noticeable amounts of copper(II) being detectable in the eluate.
3. By using silica gel, the copper(II) content in the eluting agent can be increased beyond the minimum content of 20 ppm.

EXAMPLE 4

Generator columns were prepared in accordance with the process of European Pat. No. B-0,014,957. However, some additionally contained silica gel as the bottom layer. These were charged with Mo-99 and eluted each working day with physiological sodium chloride solution. The results are shown in Table 4.

TABLE 4

| | Measurement parameter | Elution days 1 Monday | 2 Tuesday | 3 Wednesday | 4 Thursday | 5 Friday | 6 Monday | 7 Tuesday | 8 Wednesday | 9 Thursday |
|---|---|---|---|---|---|---|---|---|---|---|
| Generator according to European Patent B-14,957 | Yield of Tc-99m | 88.9 | 81.8 | 81.9 | 80.9 | 80.0 | 88.3 | 80.7 | 80.7 | 81.3 |
| 401 mCi of Mo-99 on the CD | Mo-99 (ppm) | 6 | 7 | 6 | 6 | 6 | 5 | 5 | 5 | 5 |
| Generator according to European Patent B-14,957, but with silica gel | Yield of Tc-99m | 86.7 | 79.9 | 79.6 | 79.3 | 78.8 | 87.1 | 78.4 | 77.6 | 77.1 |
| 680 mCi of Mo-99 on the CD | Mo-99 (ppm) | <1 | <1 | <1 | <1 | <1 | <1 | <1 | <1 | <1 |

CD = Calculation day = elution day No. 1, Monday

Table 4 shows the reduction in the Mo-99 content in the eluate also using the embodiment according to European Pat. No. B-0,014,957. Cu(II) was not to be found in any eluate.

We claim:

1. A technetium-99m generator comprising molybdenum-99 adsorbed on a carrier capable of binding said molybdenum-99 and copper(II) ions, at least one of the carrier materials being either silica gel modified with amino groups or a magnesium silicate.

2. A generator as claimed in claim 1, wherein the carrier material consists of said silica gel modified with amino groups.

3. A generator as claimed in claim 1 which contains aluminum oxide as one of the carrier materials.

4. A generator as claimed in claim 1, wherein the carrier material consists essentially of aluminum oxide and silica gel modified with amino groups.

5. A generator as claimed in claim 4 which additionally contains a magnesium silicate.

6. A generator as claimed in claim 1, wherein the carrier material consists essentially of aluminum oxide and a magnesium silicate.

7. A generator as claimed in claim 1 which comprises an elution column wherein the carrier to which the molybdenum is adsorbed forms—in the direction of the elution—the top layer and the magnesium silicate forms the lower layer.

8. A generator as claimed in claim 7, wherein the lower layer also contains silica gel modified with amino groups.

9. A generator as claimed in claim 1, which comprises an elution column wherein—in the direction of the elution—the top layer is aluminum oxide having adsorbed to it molybdenum-99 and copper(II) ions, a middle layer is aluminum oxide and the lower layer is a magnesium silicate.

10. A generator as claimed in claim 1, which comprises an elution column wherein—is the direction of the elution—the top layer is aluminum oxide having adsorbed to it molybdenum-99 and copper(II) ions, a middle layer is aluminum oxide and the lower layer is silica gel modified with amino groups.

11. In a process for preparing technetium-99 by eluting a generator containing molybdenum-99 adsorbed on a carrier material with an aqueous solution containing copper(II) ions the improvement comprising at least one of the carrier materials being either silica gel modified with amino groups or a magnesium silicate.

12. A process as claimed in claim 11, wherein the carrier material consists of said silica gel modified with amino groups.

13. A process as claimed in claim 11 which contains aluminum oxide as one of the carrier materials.

14. A process as claimed in claim 11, wherein the carrier material consists essentially of aluminum oxide and silica gel modified with amino groups.

15. A process as claimed in claim 14 which additionally contains a magnesium silicate.

16. A process as claimed in claim 11, wherein the carrier material consists essentially of aluminum oxide and a magnesium silicate.

17. A process as claimed in claim 11 which comprises eluting a column wherein the carrier to which the molybdenum is adsorbed forms—in the direction of the elution—the top layer and the magnesium silicate forms the lower layer.

18. A process as claimed in claim 17, wherein the lower layer also contains silica gel modified with amino groups.

19. A process as claimed in claim 11, which comprises eluting a column wherein—in the direction of the elution—the top layer is alumInum oxide having adsorbed to it molybdenum-99 and copper(II) ions, a middle layer is aluminum oxide and the lower layer is a magnesium silicate.

20. A process as claimed in claim 11, which comprises eluting a column wherein—in the direction of the elution—the top layer is aluminum oxide having adsorbed to it molybdenum-99 and copper(II) ions, a middle layer is aluminum oxide and the lower layer is silica gel modified with amino groups.

* * * * *

UNITED STATES PATENT AND TRADEMARK OFFICE
CERTIFICATE OF CORRECTION

PATENT NO. : 4,837,110

DATED : June 6, 1989

INVENTOR(S) : LUDWIG KUHLMANN et al.

It is certified that error appears in the above-identified patent and that said Letters Patent is hereby corrected as shown below:

In claim 10, column 7, line 29, delete "is" and substitute therefor --in--.

In claim 19, column 8, line 27, delete "alumInum" and substitute therefor --aluminum--.

Signed and Sealed this

Thirty-first Day of July, 1990

*Attest:*

HARRY F. MANBECK, JR.

*Attesting Officer* — *Commissioner of Patents and Trademarks*